(12) United States Patent
Smith et al.

(10) Patent No.: US 10,414,873 B2
(45) Date of Patent: *Sep. 17, 2019

(54) ORGANOPOLYSILOXANE POLYMERS

(71) Applicant: The Procter & Gamble Company, Cincinnati, OH (US)

(72) Inventors: Steven Daryl Smith, Fairfield, OH (US); Robert Joseph McChain, Cincinnati, OH (US); Yonas Gizaw, West Chester, OH (US); Rajan Keshav Panandiker, West Chester, OH (US); Carola Barrera, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/604,776

(22) Filed: Jan. 26, 2015

(65) Prior Publication Data
US 2015/0148511 A1    May 28, 2015

Related U.S. Application Data

(63) Continuation of application No. PCT/US2013/052585, filed on Jul. 29, 2013.

(51) Int. Cl.
| | |
|---|---|
| *C08G 77/388* | (2006.01) |
| *A61K 8/898* | (2006.01) |
| *C08G 77/385* | (2006.01) |
| *C08L 83/08* | (2006.01) |
| *A61Q 5/02* | (2006.01) |
| *A61Q 5/12* | (2006.01) |
| *A61Q 19/00* | (2006.01) |
| *C11D 3/37* | (2006.01) |

(52) U.S. Cl.
CPC ............ *C08G 77/388* (2013.01); *A61K 8/898* (2013.01); *A61Q 5/02* (2013.01); *A61Q 5/12* (2013.01); *A61Q 19/00* (2013.01); *C08G 77/385* (2013.01); *C08L 83/08* (2013.01); *C11D 3/3742* (2013.01); *A61K 2800/10* (2013.01); *A61K 2800/5426* (2013.01)

(58) Field of Classification Search
None
See application file for complete search history.

(56) References Cited

U.S. PATENT DOCUMENTS

| | | |
|---|---|---|
| 3,560,543 A | 2/1971 | Plueddemann |
| 4,200,724 A | 4/1980 | Darms et al. |
| 4,293,397 A | 10/1981 | Sato |
| 4,533,714 A | 8/1985 | Sebag et al. |
| 4,833,225 A | 5/1989 | Schaefer et al. |
| 5,300,167 A | 4/1994 | Nohr et al. |
| 5,358,667 A | 10/1994 | Bergmann |
| 5,476,660 A | 12/1995 | Somasundaran |
| 5,659,001 A | 8/1997 | De La Croi Habimana et al. |
| 5,925,341 A | 7/1999 | Cervantes et al. |
| 6,093,240 A | 7/2000 | Matsumura et al. |
| 6,201,058 B1 | 3/2001 | Mahr et al. |
| 6,338,855 B1 | 1/2002 | Albacarys |
| 6,395,858 B1 | 5/2002 | Mack et al. |
| 6,491,838 B1 | 12/2002 | Standke et al. |
| 6,515,095 B1 † | 2/2003 | Omura |
| 6,641,870 B2 | 11/2003 | Bartkowiak et al. |
| 6,833,344 B2 | 12/2004 | Boutique |
| 6,878,770 B2 | 4/2005 | Herzig |
| 6,903,061 B2 | 6/2005 | Masschelein |
| 7,118,057 B2 | 10/2006 | Hao |
| 7,217,777 B2 | 5/2007 | Lange et al. |
| 7,294,612 B2 | 11/2007 | Popplewell et al. |
| 7,514,091 B2 | 4/2009 | Restle et al. |
| 7,563,856 B2 | 7/2009 | Lange |
| 7,563,857 B2 | 7/2009 | Lange et al. |
| 7,871,972 B2 | 1/2011 | Sengupta |
| 7,888,306 B2 | 2/2011 | Sengupta |
| 8,158,572 B2 | 4/2012 | Schubert |
| 8,367,791 B2 | 2/2013 | Byrd et al. |
| 8,440,174 B2 | 5/2013 | Panandiker |
| 2003/0147842 A1 | 8/2003 | Restle et al. |
| 2004/0029981 A1* | 2/2004 | Herzig ................... C03C 17/30 516/55 |
| 2004/0048996 A1 | 3/2004 | Lange |
| 2004/0092424 A1 | 5/2004 | Boutique et al. |
| 2004/0092425 A1 | 5/2004 | Boutique et al. |

(Continued)

FOREIGN PATENT DOCUMENTS

| | | |
|---|---|---|
| CN | 101956324 | 1/2011 |
| JP | Hei 07-053330 | 2/1995 |

(Continued)

OTHER PUBLICATIONS

Article entitled "Hard Vs. Soft Quat" authored by O'Lenick and published in Cosmetics and Toiletries (Oct. 2008).*
International Search Report and Written Opinion dated Oct. 15, 2013, 9 pgs.
International Search Report and Written Opinion dated Oct. 30, 2013, 8 pgs.
International Search Report and Written Opinion dated Oct. 30, 2013, 9 pgs.

(Continued)

*Primary Examiner* — Marc S Zimmer
(74) *Attorney, Agent, or Firm* — James E Oehlenschlager; Jason J Camp

(57) ABSTRACT

Inventive organopolysiloxanes and consumer product compositions comprising such organopolysiloxanes. Such compositions can deposit effectively onto target substrates to deliver consumer-desired benefits such as conditioning, anti-wrinkle, softness, and anti-static.

51 Claims, No Drawings

(56) References Cited

U.S. PATENT DOCUMENTS

| | | |
|---|---|---|
| 2004/0138400 A1 | 7/2004 | Lange |
| 2005/0009721 A1 | 1/2005 | Delplancke et al. |
| 2005/0170994 A1 | 8/2005 | Casado-Dominguez et al. |
| 2006/0235181 A1 | 10/2006 | Lange et al. |
| 2007/0041929 A1 | 2/2007 | Torgerson |
| 2007/0041930 A1 | 2/2007 | Meder et al. |
| 2009/0142293 A1 | 6/2009 | Wagner et al. |
| 2010/0041583 A1 | 2/2010 | Ponder et al. |
| 2010/0215604 A1 | 8/2010 | Van Flordrop et al. |
| 2010/0247472 A1 | 9/2010 | Sau |
| 2011/0135588 A1 | 6/2011 | Uehara |
| 2012/0037040 A1 | 2/2012 | Standke et al. |
| 2012/0276175 A1 | 11/2012 | Dihora |
| 2014/0020188 A1 | 1/2014 | Gizaw et al. |
| 2014/0024780 A1 | 1/2014 | Benlahmar et al. |
| 2014/0030206 A1 | 1/2014 | Smith et al. |
| 2014/0128521 A1 * | 5/2014 | Sekiya .................. D21H 17/59 524/114 |
| 2014/0206805 A1 | 7/2014 | Sekiya et al. |
| 2015/0225313 A1 | 8/2015 | Schmidt et al. |
| 2015/0307417 A1 | 10/2015 | Schmidt et al. |

FOREIGN PATENT DOCUMENTS

| | | | |
|---|---|---|---|
| JP | Hei 07-053331 | | 2/1995 |
| JP | Hei 07-053332 | | 2/1995 |
| JP | 2002-308723 A | * | 10/2002 |
| JP | A-2002-308723 | | 10/2002 |
| JP | A-2002-308991 | | 10/2002 |
| JP | Hei 05-320349 | | 10/2013 |
| WO | WO9811870 A1 | | 3/1998 |
| WO | WO9932539 A1 | | 7/1999 |
| WO | WO 2000/71806 | | 11/2000 |
| WO | WO 2002/018528 | | 3/2002 |
| WO | WO 2004/041987 | | 5/2004 |
| WO | WO 2005/009721 A1 | | 2/2005 |
| WO | WO 2011/123727 A | | 10/2011 |
| WO | WO 2014/018985 | | 1/2014 |

OTHER PUBLICATIONS

International Search Report and Written Opinion dated Oct. 18, 2013, 9 pgs.

U.S. Appl. No. 14/604,778, filed Jan. 26, 2015, Steven Daryl Smith et al.

U.S. Appl. No. 14/604,779, filed Jan. 26, 2015, Yonas Gizaw et al.

U.S. Appl. No. 14/604,781, filed Jan. 26, 2015, Carola Barrera et al.

U.S. Appl. No. 14/604,782, filed Jan. 26, 2015, Carola Barrera et al.

\* cited by examiner

† cited by third party

ORGANOPOLYSILOXANE POLYMERS

FIELD OF THE INVENTION

The present invention relates to inventive organopolysiloxane polymers. It also relates to consumer product compositions comprising the inventive organopolysiloxane polymers and to methods of making and use.

BACKGROUND OF THE INVENTION

Cationic conditioning polymers meant for deposition onto negatively charged surfaces, such as fabric, skin, or hair, are included in many common consumer product compositions. Such products can provide consumer-desired benefits such as softness, lubricity, hand, anti-wrinkle, hair conditioning, frizz control, skin moisturization, and color protection. The effectiveness of any particular conditioning polymer depends not only upon the chemical and physical properties of the conditioning polymer itself, but also upon those of the targeted surface and the product formulation in which the conditioning polymer is delivered.

Many consumer products containing cationic conditioning polymers are in the form of aqueous-based rinse-off compositions, such as hair shampoos, body washes, laundry detergents, and fabric softeners. Despite the popularity of these rinse-off compositions, such product forms frequently experience difficulties effectively depositing these cationic conditioning polymers, which are typically hydrophobic, onto the target surfaces. Incorporating these conditioners into aqueous-based products often results in the conditioner being preferentially rinsed away from the intended site of deposition, rather than effectively deposited. This problem is particularly pronounced in the context of cleansing compositions containing surfactant, especially those containing anionic surfactant.

Anionic surfactants can interfere with deposition by forming complexes/precipitates with the cationic conditioning polymers. The higher the concentration of anionic surfactant, the more difficult it becomes to deposit cationic benefit actives. This leads to non-cost-effective use and waste of materials. Further, even if an acceptable level of deposition is attained, these formulations may lack shelf-stability due to flocculation and precipitation, making them unacceptable as consumer products.

Several materials exist in the art, but are not wholly satisfactory. For example, the material described by Ono (WO 99/32539) comprises functionalized end groups having heteroatoms such as oxygen, nitrogen, sulfur, or halogens. These functionalized end groups can lead to undesirable reactions that pose stability issues for compositions comprising these materials. For instance, Ono's silicones can react further through these end groups, leading to further condensation and/or polymerization of the silicones in the compositions during storage.

Also known in the art are quaternized silicones that include alkylene oxide units, such as those described by Masschelein (U.S. Pat. No. 6,903,061). The quaternized silicones described by Masschelein may be too water soluble for a given application, and thus can have a reduced capacity as conditioning polymers, since these materials tend to partition into water at a higher than desired level rather than deposit on the target substrate. Further, when these materials are used as the conditioning active, they can have an undesirable feel because of their high permeability to water and water vapor. Additionally, because of the potential for variability in the alkylene oxide moiety, these materials can be difficult to formulate reproducibly. This can limit the desired degree of functionality in a silicone material. It would desirable to have a material the provides greater flexibility via the level of quaternization. Similarly, the ethoxylated quaternized silicone materials disclosed by Boutique (U.S. Pat. No. 6,833,344) suffer from many of the same inadequacies of those described by Masschelein.

There is still a need to provide cationic conditioning polymers that are suitable for use in a wide range of consumer product applications. The present invention provides cationic conditioning polymers and consumer product compositions comprising conditioning polymers that can effectively deposit and provide conditioning benefits to negatively charged substrates while avoiding the aforementioned disadvantages.

SUMMARY OF THE INVENTION

The present invention attempts to solve one or more of the aforementioned needs by providing, in one aspect, inventive cationic organosilicone polymers that are suitable for use in a wide range of consumer product compositions. The inventive polymer is functionalized to favorably interact with the targeted substrate and product composition to deliver desired deposition and conditioning benefits, as well as desired shelf-stability.

Without being bound by theory, when cationic charge that could otherwise facilitate hydrophobic benefit agent deposition is randomly distributed along the length of the benefit agent polymer, the charge can be too highly dispersed to adequately facilitate deposition. The inventive polymer's charge density can be custom-tailored (e.g., higher charge density) to enhance deposition and conditioning performance in different use environments. Further, by varying the inventive polymer's level of hydrophobic substitution and/or the degree of ethoxylation, propoxylation, and alkoxylation, the inventive polymer can be formulated into a desirably stable composition for a variety of use environments. By controlling charge density and hydrophobic substitution and/or degree of ethoxylation, propoxylation, and more generally alkoxylation, the inventive polymer can be custom-tailored for a variety of product formulations and uses.

DETAILED DESCRIPTION OF THE INVENTION

I. Definitions

As used herein "consumer product" means baby care, personal care, fabric & home care, family care (e.g., facial tissues, paper towels), feminine care, health care, beauty care and like products generally intended to be used or consumed in the form in which they are sold. Such products include but are not limited to diapers, bibs, and wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, and tooth whitening.

As used herein, the term "cleansing and/or treatment composition" is a subset of consumer products that includes, unless otherwise indicated, personal care, fabric care, and home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening. The care agents can advantageously be used in household polishes and cleaners for floors and countertops to provide benefits such as enhanced shine. Care agents in fabric softeners can help preserve "newness" because of their softening properties, and those having elasticity can help smooth out wrinkles. The care agents can also enhance shoe cleaning and polishing products.

As used herein, the term "personal care cleansing and/or treatment composition" is a subset of cleaning and treatment compositions that includes, unless otherwise indicated, products for treating hair, including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products; liquid cleaning and disinfecting agents including antibacterial hand-wash types, cleaning bars, mouthwashes, denture cleaners, and dentifrice cleansers; hair shampoos and hair-rinses; shower gels, fine fragrances, and foam baths; substrate-laden products such as dry and wetted wipes and pads, nonwoven substrates, and sponges; as well as sprays and mists all for consumer or/and institutional use; and/or methods relating to oral care including toothpastes, tooth gels, tooth rinses, denture adhesives, and tooth whitening.

As used herein, the term "fabric and/or hard surface cleansing and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products, as applicable, may be in standard, concentrated or even highly concentrated form even to the extent that such products may in certain aspects be non-aqueous.

As used herein, articles such as "a" and "an" are understood to mean one or more of what is claimed or described.

As used herein, the terms "include", "contain", and "have" are non-limiting and do not exclude other components or features beyond those expressly identified in the description or claims.

As used herein, the terms "treatment agent", "benefit agent", "active", "active agent", and/or "care agent" and the like are used interchangeably to mean materials that can impart desirable aesthetic and/or functional properties (e.g., conditioning benefits such as softening or freshening) to a substrate. For example, the inventive organopolysiloxane polymer of the present invention can be used as a conditioning agent to impart conditioning benefits to substrates.

As used herein, the terms "conditioning agent" and "conditioning aid" are used interchangeably to refer to a material that delivers desirable conditioning effects (e.g., benefits such as softening or freshening) to a substrate. Conditioning agents are a type of treatment agent.

As used herein, the term "conditioning polymer" means a polymer that delivers desirable conditioning effects (e.g., softening or freshening) to a substrate.

As used herein, the term "substrate" is synonymous and used interchangeably with the terms "situs" and "surface". Non-limiting examples of substrates include paper products, fabrics, garments, hard surfaces, hair, and skin.

As used herein, "targeted substrate" means a substrate, or the relevant portion of a substrate, upon which deposition is intended.

As used herein, a "deposition aid" is a material that assists another material (e.g., a benefit agent) to deposit (e.g., adhere) to a targeted substrate. The term "deposition aid" is broad enough to encompass both polymeric deposition aids (i.e. "deposition polymer") and non-polymeric deposition aids.

As used herein, "adjunct" means an optional material that can be added to a composition to complement the aesthetic and/or functional properties of the composition.

As used herein, "auxiliary composition" refers to one or more compositions that when combined with a benefit agent emulsion of the present invention, form a consumer product composition. The auxiliary composition may be in the form of one or more ingredients or ingredient combinations.

As used herein, "carrier" means an optional material, including but not limited to a solid or fluid, that can be combined with a benefit agent (e.g., conditioning polymers) to facilitate delivery and/or use of the benefit agent.

As used herein, the term "solid" includes granular, powder, bar and tablet product forms.

As used herein, the term "fluid" includes liquid, gel, paste and gas product forms including unitized-dose forms that generally include a fluid composition enclosed in a pouch or other delivery vehicle.

As used herein, the term "particle" includes solid and semi-solid particles, as well as emulsion droplets.

Unless otherwise indicated, all percentages and ratios herein are calculated based on weight.

All percentages and ratios are calculated based on weight of the total composition unless otherwise indicated.

Unless specified otherwise, all molecular weights are given in Daltons.

Unless otherwise indicated, all molecular weights are weight average molecular weights as determined by size exclusion chromatography using a MALS detector (SEC-MALS), as is commonly known by those skilled in the art. A MALS detector (Multi-Angle Light Scattering Detector, such as those manufactured by Malvern Instruments Ltd., Malvern, UK) determines absolute molecular weight, rather than relative molecular weight (i.e., determined relative to a standard).

Unless otherwise noted, all component (i.e., ingredient) or composition levels are in reference to the active portion of that component or composition, and are exclusive of impurities, for example, residual solvents or by-products, which may be present in commercially available sources of such components or compositions.

The term "charge density", as used herein, refers to the ratio of the number of positive charges on a monomeric unit of which a polymer is comprised, to the molecular weight of said monomeric unit. The charge density multiplied by the polymer molecular weight determines the number of positively charged sites on a given polymer chain. The charge density calculation can also be expressed as:

$$\text{charge density} = \frac{(\text{moles of N})(\text{charge per N})}{(\text{moles of polymer})(\text{molecular weight of the polymer})} \times 1000$$

As used herein, the term "hydrocarbon polymer radical" means a polymeric radical comprising only carbon and hydrogen.

As used herein, "ethylene moiety" means a divalent $CH_2CH_2$ moiety.

As used herein, the term "siloxyl residue" means a polydialkylsiloxane moiety.

As used herein, the nomenclature $SiO_{n/2}$ represents the ratio of oxygen and silicon atoms. For example, $SiO_{1/2}$ means that, on average, one oxygen atom is shared between two silicon atoms. Likewise $SiO_{2/2}$ means that, on average, two oxygen atoms are shared between two silicon atoms and $SiO_{3/2}$ means that, on average, three oxygen atoms are shared between two silicon atoms.

As used herein, the terms "substantially no", "substantially free of", and/or "substantially free from" mean that the indicated material is at the very minimum not deliberately added to the composition to form part of it, or, preferably, is not present at analytically detectable levels. It is meant to include compositions whereby the indicated material is present only as an impurity in one of the other materials deliberately included.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

II. Organopolysiloxane Polymers

The present invention provides a blocky cationic organopolysiloxane having the formula:

wherein:
M=$[SiR_1R_2R_3O_{1/2}]$, $[SiR_1R_2G_1O_{1/2}]$, $[SiR_1G_1G_2O_{1/2}]$, $[SiG_1G_2G_3O_{1/2}]$, or combinations thereof;
D=$[SiR_1R_2O_{2/2}]$, $[SiR_1G_1O_{2/2}]$, $[SiG_1G_2O_{2/2}]$ or combinations thereof;
T=$[SiR_1O_{3/2}]$, $[SiG_1O_{3/2}]$ or combinations thereof;
Q=$[SiO_{4/2}]$;
w=is an integer from 1 to (2+y+2z);
x=is an integer from 5 to 15,000;
y=is an integer from 0 to 98;
z=is an integer from 0 to 98;
$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy, $C_1$-$C_{32}$ alkylamino, and $C_1$-$C_{32}$ substituted alkylamino;
at least one of M, D, or T incorporates at least one moiety $G_1$, $G_2$ or $G_3$; and $G_1$, $G_2$, and $G_3$ are each independently selected from the formula:

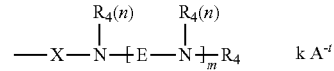

wherein:
X comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if X does not comprise a repeating alkylene oxide moiety then X can further comprise a heteroatom selected from the group consisting of P, N and O;
N=a nitrogen atom;
$R_4$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl;

E comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide and ring-opened glycidyl, with the proviso that if E does not comprise a repeating alkylene oxide moiety then E can further comprise a heteroatom selected from the group consisting of P, N, and O;

m is an integer independently selected from 2 to 100;

n is an integer independently selected from 1 or 2;

when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$; and further wherein at least one E does not comprise an ethylene moiety;

where t is an integer independently selected from 1, 2, or 3; and $k \le (m/t)+1$ such that the total number of cationic charges balances the total number of anionic charges in the organopolysiloxane molecule.

In one embodiment, there are no E moieties that are ethylene moieties. The organopolysiloxane can have a charge density of from 0.04 meq/g to 12 meq/g, or from 0.04 meq/g to 4 meq/g; or from 1 meq/g to 12 meq/g. In some embodiments, w is an integer from 2 to 50, and in others w is equal to 2. In particular embodiments, x is an integer from 10 to 4,000, or from 40 to 2,000. In one embodiment, w is equal to 2, x is an integer from 20 to 1,000, and y and z are 0.

Each X can be a divalent radical independently selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl. Alternatively, each X can be a divalent radical independently selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, and $C_6$-$C_{32}$ substituted arylalkylene.

$A^{-t}$ can be selected from the group consisting of $Cl^-$, $Br^-$, $I^-$, methylsulfate, toluene sulfonate, carboxylate, phosphate, hydroxide, acetate, formate, carbonate, nitrate, and combinations thereof; or alternatively from the group consisting of $Cl^-$, $Br^-$, $I^-$, methylsulfate, toluene sulfonate, carboxylate, phosphate and combinations thereof.

Each E can be an identical or different radical. In some embodiments, each E is a different radical. Each E can be a divalent radical independently selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, and $C_1$-$C_{32}$ substituted alkyleneamino; or each E can be a divalent radical independently selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, and $C_6$-$C_{32}$ substituted arylalkylene.

In some embodiments, at least one E is independently selected from the group consisting of:

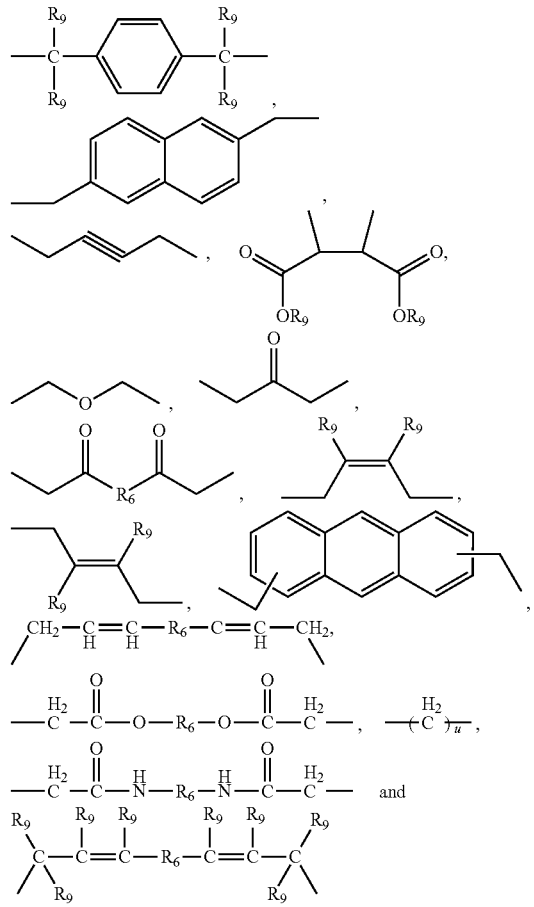

wherein:

$R_6$ comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if $R_6$ does not comprise a repeating alkylene oxide moiety then $R_6$ can further comprise a heteroatom selected from the group consisting of P, N, and O;

$R_9$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl; and u is an integer independently selected from 3 to 32.

At least one E radical can be an ethylene radical. At least one E comprises 3 or more carbon atoms. Each $R_4$ can be different radicals, and in some embodiments at least one $R_4$ is a methyl radical.

In one embodiment, $G_1$, $G_2$ and $G_3$ are identical; in another embodiment, $G_1$ and $G_2$ are the same while $G_3$ is different; and in another embodiment, each of $G_1$, $G_2$, and $G_3$ are different. For at least one of $G_1$, $G_2$ or $G_3$, m can be an integer independently selected from 2 to 50, or from 2 to 25, or from 2 to 10. Or, for at least one of $G_1$, $G_2$ or $G_3$, k can be an integer independently selected from 0 to 101, or from 2 to 50. In at least one embodiment, y=z=0. In some embodiments, from 50% to 100% of the amines present in the molecule can be quaternized, or from 70% to 100%, or from 90% to 100%.

One skilled in the art will recognize that the blocky organopolysiloxane of the present invention encompasses a plethora of different embodiments. To this end, when both y and z equal zero, the blocky organopolysiloxane of the present invention can be represented by the formula:

$$M_w D_x$$

where:
M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;
D=[SiR$_1$R$_2$O$_{2/2}$];
w=is an integer from 1 to 2;
x=is an integer from 5 to 15,000;
R$_1$, R$_2$ and R$_3$ are each independently selected from the group consisting of H, OH, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy, C$_1$-C$_{32}$ alkylamino, and C$_1$-C$_{32}$ substituted alkylamino;
at least one of M or D incorporates at least one moiety G$_1$, G$_2$ or G$_3$, and G$_1$, G$_2$, and G$_3$ are each independently selected from:

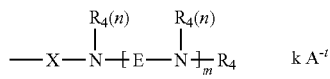

wherein:
X comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide and ring-opened glycidyl, with the proviso that if X does not comprise a repeating alkylene oxide moiety then X can further comprise a heteroatom selected from the group consisting of P, N, and O;
N=a nitrogen atom;
R$_4$ comprises identical or different monovalent radicals selected from the group consisting of H, C$_1$-C$_{32}$ alkyl, C$_1$-C$_{32}$ substituted alkyl, C$_5$-C$_{32}$ or C$_6$-C$_{32}$ aryl, C$_5$-C$_{32}$ or C$_6$-C$_{32}$ substituted aryl, C$_6$-C$_{32}$ alkylaryl, and C$_6$-C$_{32}$ substituted alkylaryl;
E comprises a divalent radical selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl, with the proviso that if E does not comprise a repeating alkylene oxide moiety then E can further comprise a heteroatom selected from the group consisting of P, N, and O;
m is an integer independently selected from 2 to 100;
n is an integer independently selected from 1 or 2; and
when at least one of G$_1$, G$_2$, or G$_3$ is positively charged, A$^{-t}$ is a suitable charge balancing anion or anions such that the total charge, k, of the charge-balancing anion or anions is equal to and opposite from the net charge on the moiety G$_1$, G$_2$ or G$_3$; and further wherein at least one E does not comprise an ethylene moiety;
where t is an integer independently selected from 1, 2, or 3; and k≤(m/t)+1
such that the total number of cationic charges balances the total number of anionic charges in the organopolysiloxane molecule.

The organopolysiloxane can have a charge density of from 0.04 meq/g to 12 meq/g, or from 0.04 meq/g to 4 meq/g, or from 1 meq/g to 12 meq/g. In one aspect, w can be equal to 2. In one embodiment, x is an integer from 10 to 4,000, or from 40 to 2,000.

Further, each X can be a divalent radical independently selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, C$_1$-C$_{32}$ substituted alkyleneamino, ring-opened epoxide, and ring-opened glycidyl; alternatively each X can be a divalent radical independently selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, and C$_6$-C$_{32}$ substituted arylalkylene.

Each A$^{-t}$ can be independently selected from the group consisting of Cl$^-$, Br$^-$, I$^-$, methylsulfate, toluene sulfonate, carboxylate, phosphate, hydroxide, acetate, formate, carbonate, nitrate, and combinations thereof; or from the group consisting of Cl$^-$, Br$^-$, I$^-$, methylsulfate, toluene sulfonate, carboxylate, phosphate, and combinations thereof.

Each E can be an identical or different radical. In some embodiments, each E is a different radical. Each E can be a divalent radical independently selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, C$_6$-C$_{32}$ substituted arylalkylene, C$_1$-C$_{32}$ alkoxy, C$_1$-C$_{32}$ substituted alkoxy, C$_1$-C$_{32}$ alkyleneamino, and C$_1$-C$_{32}$ substituted alkyleneamino; or each E can be a divalent radical independently selected from the group consisting of C$_1$-C$_{32}$ alkylene, C$_1$-C$_{32}$ substituted alkylene, C$_5$-C$_{32}$ or C$_6$-C$_{32}$ arylene, C$_5$-C$_{32}$ or C$_6$-C$_{32}$ substituted arylene, C$_6$-C$_{32}$ arylalkylene, and C$_6$-C$_{32}$ substituted arylalkylene.

In some embodiments, at least one E is independently selected from the group consisting of:

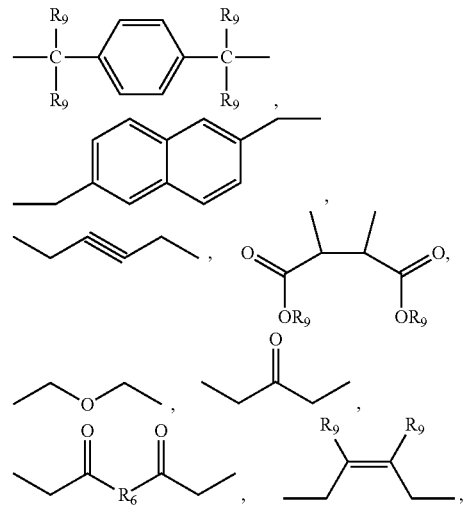

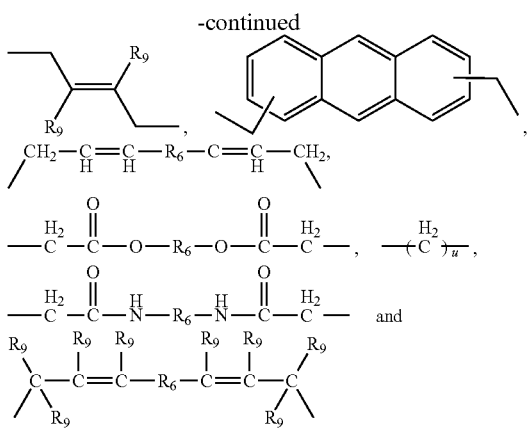

wherein:

$R_6$ comprises a divalent radical selected from the group consisting of $C_1$-$C_{32}$ alkylene, $C_1$-$C_{32}$ substituted alkylene, $C_5$-$C_{32}$ or $C_6$-$C_{32}$ arylene, $C_5$-$C_{32}$ or $C_6$-$C_{32}$ substituted arylene, $C_6$-$C_{32}$ arylalkylene, $C_6$-$C_{32}$ substituted arylalkylene, $C_1$-$C_{32}$ alkoxy, $C_1$-$C_{32}$ substituted alkoxy, $C_1$-$C_{32}$ alkyleneamino, $C_1$-$C_{32}$ substituted alkyleneamino, ring-opened epoxide, and ring-opened glycidyl, with the proviso that if $R_6$ does not comprise a repeating alkylene oxide moiety then $R_6$ can further comprise a heteroatom selected from the group consisting of P, N, and O;

$R_9$ comprises identical or different monovalent radicals selected from the group consisting of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted alkylaryl; and u is an integer independently selected from 3 to 32.

Further, in some embodiments, at least one E radical is an ethylene radical. At least one E radical can comprise 3 or more carbon atoms. In some embodiments, each of $R_4$ are different radicals. In other embodiments, at least one $R_4$ is a methyl radical.

In one embodiment, E is a primary alkyl chain having 3 or more carbon atoms, or 4 or more carbon atoms, or 5 or more carbon atoms, or from 4 to 32 carbon atoms. Without being limited by theory, it is believed that in embodiments where E is a primary alkyl chain having exactly 2 carbon atoms, the moiety G can be unstable relative to the potential for an elimination reaction. This is because an undesirable elimination reaction is likely to take place, due to an unshared electron pair reacting to create an alkene. Thus, materials having fewer than 3 carbon atoms as the E moiety can be unstable and not preferred.

In another embodiment, the moiety E can be independently selected from different groups of different length to control the spacing and density of the charges along the chain. In certain applications, it can be desirable to have these charges closely spaced, and in other applications it can be desirable to have these charges spaced farther apart. The charged moiety G can be separate from the silicone portion of the organopolysiloxane, and more specifically, disposed at the terminal ends of the siloxane moiety. Without being bound by theory, it is believed that maintaining the charges in a "blocky" fashion disposed at the ends of a terminal siloxane moiety, allows the siloxane moiety to project further out from the surface of the treated substrate, resulting in a more lubricious, softer feel for the treated substrate.

Charged organopolysiloxanes can also be difficult to formulate, particularly into aqueous products, where they generally need to be emulsified. The use of longer spacers enables a less concentrated, more dispersed charge density into the aqueous medium of aqueous compositions comprising the organopolysiloxanes. This can result in better dispersion of the organopolysiloxanes during formulation. Longer spacers allow the charge to be more dispersed throughout the molecule. In one embodiment, X is a hydrocarbon moiety not comprising any heteroatoms (e.g., substantially free from any heteroatoms). Although not wishing to be limited by theory, the presence of reactive end groups is believed to result in unstable products that are not shelf-stable, due to their tendency to degrade or react with other materials in the composition over time or to be negatively impacted by destabilizing factors in the use environment.

In one embodiment, the terminal moieties of the organopolysiloxane are hydrocarbon groups not comprising any heteroatoms (e.g., substantially free from any heteroatoms). Without being bound by theory, it is believed that alkyl end groups of the organopolysiloxanes of the present invention are not as highly degradative or reactive, thus resulting in compositions that are more stable and have a suitably longer shelf-life.

III. Methods of Making the Organopolysiloxane

Embodiments of the present invention can be made as follows. An amount of amino silicone is added to a clean vessel under inert atmosphere. Optionally, a solvent such as isopropanol or tetrahydrofuran is added. The reaction is optionally mixed and quantities of diamine and difunctional organic compounds capable of reacting with the amino functions of the amine compounds are added, either simultaneously or sequentially. For example, the diamine may be added first and the difunctional organic compound capable of reacting with the amino function added second, to obtain the desired organopolysiloxane. Alternately, these reagents may be added in reverse order.

The reaction is run at a temperature appropriate for the reagents. For example, when the difunctional organic compound capable of reacting with the amino functions is a dichloride, the reaction may be run at relatively higher temperatures (typically above 60° C. and often above 80° C.). Alternately, when the difunctional organic compound capable of reacting with the amino functions is a dibromide, the reaction may be run at relatively lower temperatures, including at room temperature (e.g., 21° C.). Alternately, when the difunctional organic compound capable of reacting with the amino functions is an activated dichloride, the reaction may be run at relatively lower temperatures, including at room temperature (e.g., 21° C.). One of ordinary skill in the art would understand the reaction conditions suitable for the specific difunctional organic compound capable of reacting with the amino functions.

The above making process is also generally described by Lange (U.S. Pat. No. 7,563,856). One skilled in the art would understand how the general process disclosed in Lange can be reapplied to the present development in order to produce the organopolysiloxanes of the present invention.

In one embodiment, the reaction is run without the addition of solvent, resulting in a substantially solvent-free process for making the organopolysiloxane of the present invention.

In another embodiment, the reaction is run and subsequently excess amine is added. Without being bound by theory, it is believed that the excess amine will consume the reactive groups of any residual difunctional organic compounds capable of reacting with the amino functions.

In another embodiment, the reaction mixture is further reacted with an amine containing molecule. Non-limiting examples of such amines include ammonia, methylamine, dimethylamine, trimethylamine, triethylamine or ethanolamine or diethanolamine. Without being bound by theory it is believed that this further reaction caps un-reacted akyl-halide functionality.

In another embodiment, the reaction mixture is further reacted with a mono-functional organic species capable of reacting with the amine functionality of the organopolysiloxane. Non-limiting examples of such mono-functional organic species include: methyl bromide, methyl iodide, and ethylbromide. Without being bound by theory it is believed that this further reaction helps to quaternize any residual neutral amine groups of the organopolysiloxane, including the terminal amine functionality.

IV. Uses of the Organopolysiloxane Compositions

The organopolysiloxanes according to the present invention can be formulated into a variety of consumer product compositions that can be applied to substrates in order to impart consumer-desired benefits, such as conditioning. Such substrates can include fabric, non-woven materials, paper products, hard surface materials, and biological materials (e.g., keratinous materials such as hair or skin).

The consumer product compositions comprising the organopolysiloxane polymers of the present invention may be prepared by any suitable process, such as processes known by those skilled in the art. For example, the organopolysiloxane polymers can be incorporated directly into the composition's other ingredients without pre-emulsification and/or pre-mixing to form the finished products. Alternatively, the organopolysiloxane may be mixed with surfactants, solvents, suitable adjuncts, and/or any other suitable ingredients to prepare emulsions prior to compounding the finished products.

The consumer product composition can comprise one or more surfactants. The surfactants may comprise cationic, anionic, non-ionic, zwitterionic, and/or amphoteric surfactants. In one embodiment, at least one surfactant is anionic. Various forms of the consumer product composition can be aqueous or non-aqueous; in one embodiment, an aqueous composition has a pH greater than 3, or greater than 5.

The composition may also comprise at least one benefit agent. Benefit agents can be hydrophobic or hydrophilic. Useful hydrophobic benefit agents include silicones, vinyl polymers, polyethers, materials comprising a hydrocarbon wax, hydrocarbon liquids, fluid sugar polyesters, fluid sugar polyethers, and mixtures thereof. In one embodiment, the silicones that are useful as benefit agents are organosilicones. In another embodiment, the silicone benefit agent is selected from the group consisting of a polydimethylsiloxane, an aminosilicone, a cationic silicone, a silicone polyether, a cyclic silicone, a silicone resin, a fluorinated silicone, and mixtures thereof. In one embodiment, the benefit agent is a liquid at room temperature. In another embodiment, the benefit agent is a solid or semi-solid at room temperature. In one embodiment, the benefit agent is a perfume or a silicone. Further, the benefit agent may be encapsulated. In one embodiment, the benefit agent is an encapsulated perfume.

The organopolysiloxane may be pre-emulsified prior to compounding into a consumer product composition. In one embodiment, a benefit agent is included with the organopolysiloxane in the pre-emulsion. In one embodiment, the benefit agent and the organopolysiloxane mixture can form a particle in the pre-emulsion.

Materials which may be helpful in creating such emulsions include: Tergitol 15-S-5, Terigtol 15-S-12, and TMN-10. The suspensions can be made by mixing the components together using a variety of mixing devices. Examples of suitable overhead mixers include: IKA Labortechnik, and Janke & Kunkel IKA WERK, equipped with impeller blade Divtech Equipment R1342. In some cases, high shear processing is required to obtain a narrow particle size distribution. Example of a suitable high shear processing device is M-110P Microfluidizer from Microfluidics.

EXAMPLES

The following examples further describe and demonstrate exemplary embodiments within the scope of the present invention. The examples are given solely for the purpose of illustration and are not to be construed as limitations of the present invention since many variations thereof are possible without departing from the spirit and scope of the invention. Ingredients are identified by chemical name, or otherwise defined below.

Examples 1-47 (Organopolysiloxanes)

Organopolysiloxanes of the present invention are prepared as follows using the following difunctional organic compounds capable of reacting with amino functions.

Dibromo Compounds (Examples 1-15 and 28-30 and 33-34):

To a clean vessel is added the quantity of silicones (available from Gelest Co., Morrisville, Pa.) shown in Table 1 and the quantity of diamine (available from Sigma-Aldrich, Milwaukee, Wis.) shown and an amount of isopropanol (available from Sigma-Aldrich, Milwaukee, Wis.) equal to the amount of silicone. This is mixed by stirring the sample at 30 rpm for one hour and then the quantity of dibromide (available from Sigma-Aldrich, Milwaukee, Wis.) is added and mixed by stirring at 30 rpm for 2 hours at 25° C. This is followed by heating the sample at 50° C. for 16 hours.

Dichloro Compounds (Examples 16-17):

To a clean vessel is added the quantity of silicones (available from Gelest Co., Morrisville, Pa.) shown in Table 1 and the quantity of diamine (available from Sigma-Aldrich, Milwaukee, Wis.) shown. This is mixed by stirring the sample at 30 rpm for one hour and then the quantity of dichlorlide (available from Sigma-Aldrich, Milwaukee, Wis.) is added and mixed by stirring at 30 rpm for 2 hours at 25° C. This is followed by heating the sample at 85° C. for 72 hours.

Activated Dichloro Compounds (Examples 18-27 and 31-32)

To a clean vessel is added the quantity of silicones (available from Gelest Co., Morrisville, Pa.) shown in Table 1 and the quantity of diamine (available from Sigma-Aldrich, Milwaukee, Wis.) shown and an amount of isopropanol (available from Sigma-Aldrich, Milwaukee, Wis.) equal to the amount of silicone. This is mixed by stirring the sample at 30 rpm for one hour and then the quantity of activated dichloride (available from Sigma-Aldrich, Milwaukee, Wis.) is added and mixed by stirring at 30 rpm for 2 hours at 25° C. This is followed by heating the sample at 50° C. for 16 hours.

Dibromo Compounds (Examples 35-36) (Solvent Free)

To a clean vessel is added the quantity of silicones (available from Gelest Co., Morrisville, Pa.) shown in Table 1 and the quantity of diamine (available from Sigma-Aldrich, Milwaukee, Wis.) shown. This is mixed by stirring the sample at 20 rpm for one hour and then the quantity of dibromide (available from Sigma-Aldrich, Milwaukee, Wis.) is added and mixed by stirring at 30 rpm for 2 hours at 25° C. This is followed by heating the sample at 50° C. for 16 hours.

Activated Dichloro Compounds (Examples 37-38) (Solvent Free)

To a clean vessel is added the quantity of silicones (available from Gelest Co., Morrisville, Pa.) shown in Table 1 and the quantity of diamine (available from Sigma-Aldrich, Milwaukee, Wis.) shown. This is mixed by stirring the sample at 30 rpm for one hour and then the quantity of activated dichloride (available from Sigma-Aldrich, Milwaukee, Wis.) is added and mixed by stirring at 30 rpm for 2 hours at 25° C. This is followed by heating the sample at 50° C. for 16 hours.

Activated Dichloro Compounds (Examples 39-40) (Amine Capping)

To a clean vessel is added the quantity of silicones (available from Gelest Co., Morrisville, Pa.) shown in Table 1 and the quantity of diamine (available from Sigma-Aldrich, Milwaukee, Wis.) and an amount of isopropanol (available from Sigma-Aldrich, Milwaukee, Wis.) equal to the amount of silicone shown. This is mixed by stirring the sample at 30 rpm for one hour and then the quantity of activated dichloride (available from Sigma-Aldrich, Milwaukee, Wis.) is added and mixed by stirring at 30 rpm for 2 hours at 25° C. This is followed by heating the sample at 50° C. for 16 hours. After 16 hours, 2 grams of triethylamine (available from Sigma-Aldrich, Milwaukee, Wis.) is added and mixed by stirring at 30 rpm for 6 hours at 50° C. After 6 hours, the reaction mixture is vacuum stripped for 4 hours.

The samples in Table 1 are prepared according to the above instructions using the amounts shown. The silicone starting material for each example is a terminal amino silicone, having a propenyl moiety between the terminal silicone atom and the amine nitrogen. The difunctional organic compounds capable of reacting with the amino functions are selected from the group of dihalides selected from the group consisting of dichlorides, dibromides, and activated dichlorides. Diamines were selected from the group consisting of TMHDA (tetramethyl-hexane-diamine) and TMEDA (tetramethyl-ethane-diamine). The diamine structure of examples 1-13 and 16-17 is TMHDA. The diamine structure of examples 14-15 is TMEDA.

TABLE 1

| Example # | Amino Silicone starting material[1] | Weight (g) Silicone | Molecular Weight (Daltons) Silicone | Weight (g) Dihalide | Dihalide | Weight (g) Diamine | # Repeat Units of polyquat on each terminus |
|---|---|---|---|---|---|---|---|
| 1 | DMS-A15 | 75 g | 3000 | 12.20 g | Dibromo Hexane | 8.60 g | 1 |
| 2 | DMS-A15 | 50 g | 3000 | 20.33 g | Dibromo Hexane | 14.33 g | 2 |
| 3 | DMS-A15 | 25 g | 3000 | 20.33 g | Dibromo Hexane | 14.33 g | 5 |
| 4 | DMS-A15 | 25 g | 3000 | 40.67 g | Dibromo Hexane | 28.67 g | 10 |
| 5 | DMS-A32 | 500 g | 30000 | 2.03 g | Dibromo Hexane | 1.43 g | 0.5 |
| 6 | DMS-A32 | 500 g | 30000 | 4.07 g | Dibromo Hexane | 2.87 g | 1 |
| 7 | DMS-A32 | 250 g | 30000 | 4.07 g | Dibromo Hexane | 2.87 g | 2 |
| 8 | DMS-A32 | 100 g | 30000 | 4.07 g | Dibromo Hexane | 2.87 g | 5 |
| 9 | DMS-A32 | 1000 g | 30000 | 81.33 g | Dibromo Hexane | 57.33 g | 10 |
| 10 | DMS-A32 | 100 g | 30000 | 16.27 g | Dibromo Hexane | 11.47 g | 20 |
| 11 | DMS-A35 | 150 g | 50000 | 1.46 g | Dibromo Hexane | 1.03 g | 2 |
| 12 | DMS-A35 | 150 g | 50000 | 3.66 g | Dibromo Hexane | 2.58 g | 5 |
| 13 | DMS-A35 | 200 g | 50000 | 9.76 g | Dibromo Hexane | 6.88 g | 10 |
| 14 | DMS-A32 | 500 g | 30000 | 10.93 g | Dibromo Dodecane | 3.87 g | 2 |
| 15 | DMS-A32 | 250 g | 30000 | 3.60 g | Dibromo Butane | 1.93 g | 2 |
| 16 | DMS-A32 | 100 g | 30000 | 10.33 g | Dichloro Hexane | 11.47 g | 20 |
| 17 | DMS-A32 | 100 g | 30000 | 0.52 g | Dichloro Hexane | 0.57 g | 5 |
| 18 | DMS-A15 | 50 g | 3000 | 20.83 g | 1,4-dichloro-2-butene | 28.67 g | 5 |
| 19 | DMS-A15 | 50 g | 3000 | 41.67 g | 1,4-dichloro-2-butene | 57.33 g | 10 |
| 20 | DMS-A32 | 50 g | 30000 | 0.83 g | 1,4-dichloro-2-butene | 1.15 g | 1 |
| 21 | DMS-A32 | 50 g | 30000 | 2.08 g | 1,4-dichloro-2-butene | 2.87 g | 2.5 |
| 22 | DMS-A32 | 50 g | 30000 | 0.83 g | 1,4-dichloro-2-butene | 0.77 g | 1 |
| 23 | DMS-A32 | 50 g | 30000 | 4.17 g | 1,4-dichloro-2-butene | 3.87 g | 5 |
| 24 | DMS-A32 | 100 g | 30000 | 2.33 g | P-dichloroxylene | 2.29 g | 1 |
| 25 | DMS-A32 | 100 g | 30000 | 5.83 g | P-dichloroxylene | 5.73 g | 2.5 |
| 26 | DMS-A32 | 100 g | 30000 | 2.33 g | P-dichloroxylene | 1.55 g | 1 |
| 27 | DMS-A32 | 100 g | 30000 | 11.67 g | P-dichloroxylene | 7.73 g | 5 |
| 28 | DMS-A32 | 100 g | 30000 | 3.25 g | Dibromo hexane | 2.29 g | 2 |
| 29 | DMS-A35 | 150 g | 50000 | 2.93 g | Dibromo hexane | 2.06 g | 2 |
| 30 | DMS-A35 | 100 g | 50000 | 9.76 g | Dibromo hexane $C_6$ | 6.88 g | 10 |
| 31 | DMS-A32 | 100 g | 30000 | 2.33 g | p-dichloroxylene | 2.29 g | 2 |
| 32 | DMS-A32 | 100 g | 30000 | 1.67 g | 1,4-dichloro-2-butene | 2.29 g | 2 |
| 33 | DMS-A32 | 100 g | 30000 | 32.53 g | Dibromo hexane $C_6$ | 22.93 g | 20 |
| 34 | DMS-A35 | 100 g | 50000 | 19.52 g | Dibromo hexane $C_6$ | 13.76 | 20 |
| 35 | DMS-A32 | 250 g | 30000 | 4.07 g | Dibromo Hexane | 2.87 g | 2 |
| 36 | DMS-A32 | 100 g | 30000 | 4.07 g | Dibromo Hexane | 2.87 g | 5 |
| 37 | DMS-A32 | 100 g | 30000 | 1.67 g | 1,4-dichloro-2-butene | 2.29 g | 2 |
| 38 | DMS-A32 | 50 g | 30000 | 4.17 g | 1,4-dichloro-2-butene | 3.87 g | 5 |
| 39 | DMS-A32 | 100 g | 30000 | 1.67 g | 1,4-dichloro-2-butene | 2.29 g | 2 |
| 40 | DMS-A32 | 50 g | 30000 | 4.17 g | 1,4-dichloro-2-butene | 3.87 g | 5 |

[1] = catalogue numbers of aminosilicone starting material, available from Gelest Company, Morrisville, PA

Example 41: Preparation of Activated Terminal Chloro Functional Silicone for Use in Example 42

To a clean vessel is added 200 grams of terminal amino functional silicone (DMS-A32 available from Gelest Co., Morrisville, Pa.), 200 grams of anhydrous tertahydrofuran (available from Sigma-Aldrich, Milwaukee, Wis.) and 3 g chloro-acetyl chloride (available from Sigma-Aldrich, Milwaukee, Wis.) and 2 grams of triethylamine (available from Sigma-Aldrich, Milwaukee, Wis.). This is mixed by stirring the sample at 30 rpm for two hours and then the reaction is terminated by addition of water and extracted with 0.1N Hydrochloric acid, three times, followed by two extractions with 0.1N sodium hydroxide, followed by one extraction with deionized water. The sample is vacuum dried at 50° C. for 16 hours.

Example 42: Preparation from Activated Terminal Chloro Functional Silicone of Example 41

100 grams of activated chlorofunctional silicone prepared as in example 41 is added to a flask along with 12.61 grams of tetramethylhexanediamine (available from Sigma-Aldrich, Milwaukee, Wis.) and 10.33 grams of dichlorohexane (available from Sigma-Aldrich, Milwaukee, Wis.). This is stirred and heated to 90° C. for 72 hours.

Example 43: Preparation from Terminal Chloro Functional Silicone 100 grams of terminal chlorofunctional silicone (DMS-L21 available from Gelest Co., Morrisville, Pa.) is added to a flask along with 24.08 grams of tetramethylhexanediamine (available from Sigma-Aldrich, Milwaukee, Wis.) and 15.50 grams of dichlorohexane (available from Sigma-Aldrich, Milwaukee, Wis.). This is stirred and heated to 90° C. for 72 hours.

Example 44: Preparation from a Terminal Epoxy Silicone 100 grams of terminal epoxy functional silicone (5K) (DMS-E21 available from Gelest Co., Morrisville, Pa.) is reacted with 20.23 grams of butanediol-diglycidyl ether (available from Sigma-Aldrich, Milwaukee, Wis.) and 12.04 grams of piperazine (available from Sigma-Aldrich, Milwaukee, Wis.). The reaction is stirred at room temperature for 4 hours and then precipitated into 100 grams of water.

Example 45: Preparation from a Di-Epoxy 100 grams of terminal amine functional silicone (30K) (DMS-A32 available from Gelest Co., Morrisville, Pa.) is reacted with 13.48 grams of butanediol-diglycidyl ether (available from Sigma-Aldrich, Milwaukee, Wis.) and 5.73 grams of piperazine (available from Sigma-Aldrich, Milwaukee, Wis.). The reaction is stirred at room temperature for 4 hours and then precipitated into 100 grams of water.

Example 46: Preparation from a Terminal Epoxy Silicone and Epichlorohydrin 100 grams of terminal epoxy functional silicone (30K) is reacted with 6.17 grams of epichlorohydrin (available from Sigma-Aldrich, Milwaukee, Wis.) and 6.31 grams of piperazine (available from Sigma-Aldrich, Milwaukee, Wis.). The reaction is stirred at room temperature for 4 hours and then precipitated into 100 grams of water.

Example 47: Preparation from a Terminal Amine Silicone and Epichlorohydrin 100 grams of terminal amine functional silicone (30K) (DMS-A32) (available from Gelest Co., Morrisville, Pa.) is reacted with 6.17 grams of epichlorohydrin (available from Sigma-Aldrich, Milwaukee, Wis.) and 5.73 grams of piperazine (available from Sigma-Aldrich, Milwaukee, Wis.). The reaction is stirred at room temperature for 4 hours and then precipitated into 100 grams of water.

Molecule Examples

In the examples of Table 2 below:

$w=2$ $y=z=0$ $R_1$ and $R_2$=methyl

X=propylene $n=2$

TABLE 2

| Ex. No. | X | $R_3$ | E | $E^1$ | m | A- | k | Average Charge Density (meq/g of |
|---|---|---|---|---|---|---|---|---|
| 48 | 40 | NA | hexylene | hexylene | 2 | Br- | 3 | 1.57 |
| 49 | 40 | NA | hexylene | hexylene | 4 | Br- | 5 | 2.14 |
| 50 | 40 | NA | hexylene | hexylene | 10 | Br- | 11 | 3.07 |
| 51 | 40 | NA | hexylene | hexylene | 20 | Br- | 21 | 3.71 |
| 52 | 400 | amino-propyl | hexylene | hexylene | 0.25* | Br- | 3 | 0.097 |
| 53 | 400 | amino-propyl | hexylene | hexylene | 0.5* | Br- | 3 | 0.128 |
| 54 | 400 | NA | hexylene | hexylene | 2 | Br- | 3 | 0.19 |
| 55 | 400 | NA | hexylene | hexylene | 5 | Br- | 6 | 0.37 |
| 56 | 400 | NA | hexylene | hexylene | 10 | Br- | 11 | 0.64 |
| 57 | 400 | NA | hexylene | hexylene | 20 | Br- | 22 | 1.10 |
| 58 | 680 | NA | hexylene | hexylene | 2 | Br- | 3 | 0.12 |
| 59 | 680 | NA | hexylene | hexylene | 5 | Br- | 6 | 0.23 |
| 60 | 680 | NA | hexylene | hexylene | 10 | Br- | 11 | 0.41 |
| 61 | 400 | NA | dodecylene | ethylene | 2 | Br- | 3 | 0.20 |
| 62 | 400 | amino-propyl | butylene | ethylene | 0.5* | Br- | 3 | 0.128 |
| 63 | 400 | NA | hexylene | hexylene | 20 | Cl- | 21 | 1.10 |
| 64 | 400 | amino-propyl | hexylene | hexylene | 0.5* | Cl- | 3 | 0.128 |
| 65 | 40 | NA | butenylene | hexylene | 10 | Cl- | 11 | 3.69 |
| 66 | 40 | NA | Butenylene | hexylene | 20 | Cl- | 21 | 4.70 |
| 67 | 400 | NA | butenylene | hexylene | 2 | Cl- | 3 | 0.20 |
| 68 | 400 | NA | butenylene | hexylene | 5 | Cl- | 6 | 0.38 |
| 69 | 400 | NA | Butenylene | ethylene | 2 | Cl- | 3 | 0.19 |
| 70 | 400 | NA | butenylene | ethylene | 10 | Cl- | 11 | 0.63 |
| 71 | 400 | NA | p-xylylene | hexylene | 2 | Cl- | 2 | 0.20 |
| 72 | 400 | NA | p-xylylene | hexylene | 5 | Cl- | 6 | 0.38 |
| 73 | 400 | NA | p-xylylene | ethylene | 2 | Cl- | 3 | 0.20 |
| 74 | 400 | NA | p-xylylene | ethylene | 10 | Cl- | 11 | 0.67 |
| 75 | 400 | NA | hexylene | hexylene | 4 | Br- | 5 | 0.32 |
| 76 | 680 | NA | hexylene | hexylene | 4 | Br- | 5 | 0.19 |
| 77 | 680 | NA | hexylene | hexylene | 20 | Br- | 21 | 0.72 |
| 78 | 400 | NA | p-xylylene | hexylene | 4 | Cl- | 5 | 0.32 |
| 79 | 400 | NA | butenylene | hexylene | 4 | Cl- | 5 | 0.32 |
| 80 | 400 | NA | hexylene | hexylene | 40 | Br- | 41 | 1.76 |
| 81 | 680 | NA | hexylene | hexylene | 40 | Br- | 41 | 1.23 |
| 82 | 335 | NA | hexylene | hexylene | 4 | Br- | 5 | 0.38 |
| 83 | 335 | NA | hexylene | hexylene | 10 | Br- | 11 | 0.75 |

TABLE 2-continued

| Ex. No. | X | $R_3$ | E | $E^1$ | m | A- | k | Average Charge Density (meq/g of |
|---|---|---|---|---|---|---|---|---|
| 84 | 335 | NA | hexylene | hexylene | 20 | Br- | 21 | 1.26 |
| 85 | 335 | NA | hexylene | hexylene | 40 | Br- | 41 | 1.97 |

*When the average m is <1, then not every M group bears a charged group G. In these exemplary cases, the M groups that do not bear the charged group G will carry the group R3 as the propylamino group. Also, in these exemplary cases while the average m may be less than two each individual m for each charged group G may be greater than or equal to two.
[1] As disclosed herin, each E may be identical to or may be different from any other E. The examples of Table 2 above illustrate both of these embodiments.

End-Use Formulations:

Exemplary organopolysiloxanes of the present invention are formulated into different product chassis to make various consumer product formulations. In some embodiments, the organopolysiloxane is added to the ingredient mixture in the form of an emulsion.

Emulsion Preparation:

The following emulsions are prepared for use in the consumer product formulation examples set forth herein.

The organopolysiloxanes from Examples 56, 63, 75, 76, 80, and 82-85 above are used to make the emulsions used in making the consumer product formulation examples below.

The organopolysiloxanes from Examples 56, 63, 75, 76, 80, and 82-85 are first emulsified using a homogenizer at 3,500 rpm, and then microfluidized at 20,000 psi to obtain sub-micron size emulsions (mean particle size 250 nm, as measured using Horriba instrumentation as known in the art).

TABLE 3

| Material | % |
|---|---|
| Organopolysiloxane of Examples 56, 63, 75, 76, 80, and 82-85 in Table 2 | 20.00 |
| Tergitol 15-S-5[1] | 3.00 |
| Acetic Acid | 0.60 |
| Dilution Water | q.s. to 100% |

1.[1]Available from Sigma Aldrich

Hair Care Compositions Comprising the Organopolysiloxanes:

Examples below list non-limiting examples of hair care shampoo and conditioner compositions comprising emulsions of the organopolysiloxane conditioning polymers of the present invention.

Shampoos are prepared as follows:

| Material | % active in shampoo |
|---|---|
| Deionized Water | q.s. to 100% |
| SLE1S [1] | 10.50% |
| CMEA [2] | 0.85% |
| Na₄EDTA | 0.14% |
| NaBenzoate | 0.25% |
| Citric acid | 0.22% |
| SLS [3] | 1.50% |
| CAPB [4] | 1.00% |
| Kathon | 0.03% |
| Emulsion according to Table 3 | 5.00% |
| C500 Guar [5] | 0.25% |

[1] Sodium Laureth Sulfate, 28% active, supplier: P&G
[2] Cocoamide MEA available as Monamid CMA, 85% active, available from Goldschmidt Chemical
[3] Sodium Lauryl Sulfate, 29% active from P&G
[4] Cocoamidopropyl Betaine available as Tego ® betaine F-B, 30% active, available from Goldschmidt Chemicals
[5] Jaguar ® C500, MW - 500,000, CD = 0.7, available from Rhodia Ingredients are combined and mixed by conventional means as known by one of ordinary skill in the art.

Hair Conditioners are prepared as follows:

| Material | % active in conditioner |
|---|---|
| Cetyl Alcohol | 1.21% |
| Stearyl Alcohol | 3.00% |
| Behentrimonium methosulfate/IPA [1] | 2.47% |
| Benzyl Alcohol | 0.43% |
| Deionized Water | q.s. to 100% |
| Perfume | 0.59% |
| EDTA | 0.15% |
| Emulsions according to Table 3 | 5.00% |

[1] Behentrimonium methosulfate/Isopropyl alcohol, available as Genamin BTMS from Clariant Ingredients are combined and mixed by conventional means as known by one of ordinary skill in the art.

Top Sheets and Paper:

It can be appreciated by one of ordinary skill in the art that any of a number of means of applying the organopolysiloxane to the nonwoven can be utilized. The organopolysiloxane may be emulsified prior to application to the nonwoven, including emulsification into water or other primarily aqueous carrier. The organopolysiloxane may be dissolved in a suitable carrier prior to application to the nonwoven. The carrier may be volatile to facilitate removal of the carrier after treatment of the nonwoven. In one non-limiting example of the present invention, the organopolysiloxane of Example 56 is emulsified as described in Table 3 and air sprayed onto a 24 gsm (grams per square meter) non-woven top sheet to obtain a final coating of 5 gsm. Top sheets are air dried overnight and allowed to equilibrate in a controlled humidity room.

Fabric Care Compositions:

Examples below list non-limiting examples of Fabric Care composition comprising mulsions of the organopolysiloxane conditioning polymers of the present invention.

Heavy Duty Liquid (HDL) laundry detergent formula are prepared as follows:

| Material | % in HDL |
|---|---|
| HDL AE1.8S Paste [1] | 26.83 |
| DTPA 50% ACTIVE [2] | 0.63 |
| HDL Brightener 15 Premix[3] | 3.03 |
| Monoethanolamine (MEA) | 2.26 |
| $C_{12}/C_{14}$ AMINE OXIDE [4] | 1.69 |
| Alkoxylated polyamine HOD Base [5] | 1.20 |
| CAUSTIC SODA (NaOH) | 0.53 |
| Anionic Detergent Blend MVP-2 Paste [6] | 4.25 |
| Borax Premix for HDL [7] | 6.06 |
| C11.8 HLAS [8] | 4.19 |
| CITRIC ACID SOLUTION [9] | 5.34 |
| C12-18 FATTY ACID [10] | 1.42 |
| CALCIUM FORMATE | 0.84 |
| Water | q.s. to 100% |
| Subtilisins (NFNA-HA Base)[11] - (54.5 mg/g) | 1.27 |
| MANNANASE (25.6 mg/g) | 0.06 |
| NATALASE (29.26 mg/g) | 0.31 |

-continued

| Material | % in HDL |
|---|---|
| Polyethyleneimine Ethoxylate PE-20 (ODD-Base) [12] | 1.89 |
| Emulsions according to Table 3 | 20.00 |

[1] Available from Shell Chemicals, Houston, TX
[2] Diethylenetriaminepentaacetic acid, sodium salt
[3] Available from The Procter & Gamble Company, Cincinnati, OH
[4] Available from The Procter & Gamble Company, Cincinnati, OH
[5] Available from BASF, AG, Ludwigshafen
[6] Available from The Procter & Gamble Company, Cincinnati, OH
[7] Available from Univar, Cincinnati, OH
[8] Available from Huntsman Chemicals, Salt Lake City, UT
[9] Available from Ciba Specialty Chemicals, High Point, NC
[10] Available from Enencor International, South San Francisco, CA.
[11] Available from Genencor, Rochester, NY
[12] Available from BASF, AG, Ludwigshafen Ingredients are combined and mixed by conventional means as known by one of ordinary skill in the art.
Fabric Softener compositions are prepared as follows:

| EXAMPLE COMPOSITION | 78 |
|---|---|
| Fabric Softener Active[1] | 11.0 |
| Fabric Softener Active[2] | — |
| Cationic Starch[3] | — |
| Polyethylene imine[4] | — |
| Quaternized polyacrylamide[5] | 0.2 |
| Calcium chloride | 0.15 |
| Ammonium chloride | 0.1 |
| Suds Suppressor[6] | — |
| Emulsions according to Table 3 | 15.0 |
| Perfume | 2.0 |
| Perfume microcapsule[7] | 0.75 |
| Water, suds suppressor, stabilizers, pH control agents, buffers, dyes & other optional ingredients | q.s. to 100% pH = 3.0 |

[1] N,N di(tallowoyloxyethyl) - N,N dimethylammonium chloride available from Evonik Corporation, Hopewell, VA.
[2] Reaction product of fatty acid with Methyldiethanolamine, quaternized with Methylchloride, resulting in a 2.5:1 molar mixture of N,N-di(tallowoyloxyethyl) N,N-dimethylammonium chloride and N-(tallowoyloxyethyl) N-hydroxyethyl N,N-dimethylammonium chloride available from Evonik Corporation, Hopewell, VA.
[3] Cationic starch based on common maize starch or potato starch, containing 25% to 95% amylose and a degree of substitution of from 0.02 to 0.09, and having a viscosity measured as Water Fluidity having a value from 50 to 84. Available from National Starch, Bridgewater, NJ
[4] Available from Nippon Shokubai Company, Tokyo, Japan under the trade name Epomin 1050.
[5] Cationic polyacrylamide polymer such as a copolymer of acrylamide/[2-(acryloylamino) ethyl]tri-methylammonium chloride (quaternized dimethyl aminoethyl acrylate) available from BASF, AG, Ludwigshafen under the trade name Sedipur 544.
[6] SILFOAM® SE90 available from Wacker AG of Munich, Germany
[7] Available from Appleton Paper of Appleton, WI Ingredients are combined and mixed by conventional means as known by one of ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A cationic organopolysiloxane having the formula:

wherein:
M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;
D=[SiR$_1$R$_2$O$_{2/2}$], [SiR$_1$G$_1$O$_{2/2}$], [SiG$_1$G$_2$O$_{2/2}$] or combinations thereof;
T=[SiR$_1$O$_{3/2}$], [SiG$_1$O$_{3/2}$] or combinations thereof;
Q=[SiO$_{4/2}$];
w=is an integer from 1 to (2+y+2z);
x=is an integer from 5 to 15,000;
y=is an integer from 0 to 98;
z=is an integer from 0 to 98;
R$_1$, R$_2$, and R$_3$ are each independently selected from the group consisting of H, OH, C$_1$-C$_{32}$ alkyl, C$_1$-C$_{32}$ substituted alkyl, C$_5$-C$_{32}$ aryl, C$_5$-C$_{32}$ substituted aryl, C$_6$-C$_{32}$ alkylaryl, C$_6$-C$_{32}$ substituted alkylaryl, C$_1$-C$_{32}$ alkoxy, C$_1$-C$_{32}$ substituted alkoxy, C$_1$-C$_{32}$ alkylamino, and C$_1$-C$_{32}$ substituted alkylamino;
at least one of M, D, or T incorporates at least one moiety G$_1$, G$_2$, or G$_3$; and
G$_1$, G$_2$, and G$_3$ are each independently selected from the formula:

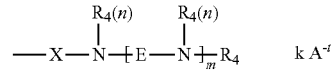

wherein:
X comprises a divalent radical selected from the group consisting of C$_1$-C$_{32}$ alkylene, C$_1$-C$_{32}$ substituted alkylene, C$_5$-C$_{32}$ arylene, C$_5$-C$_{32}$ substituted arylene, C$_6$-C$_{32}$ arylalkylene, C$_6$-C$_{32}$ substituted arylalkylene, C$_1$-C$_{32}$ alkyleneamino, C$_1$-C$_{32}$ substituted alkyleneamino, with the proviso that if X does not comprise a repeating alkylene oxide moiety then X can further comprise a heteroatom selected from the group consisting of P, N, and O;
N=a nitrogen atom;
each R$_4$ comprises identical or different monovalent radicals independently selected from the group consisting of H, C$_1$-C$_{32}$ alkyl, C$_1$-C$_{32}$ substituted alkyl, C$_5$-C$_{32}$ aryl, C$_5$-C$_{32}$ substituted aryl, C$_6$-C$_{32}$ alkylaryl, and C$_6$-C$_{32}$ substituted alkylaryl;
E comprises a divalent radical selected from the group consisting of C$_1$-C$_{32}$ alkylene, C$_1$-C$_{32}$ substituted alkylene, C$_5$-C$_{32}$ arylene, C$_5$-C$_{32}$ substituted arylene, C$_6$-C$_{32}$ arylalkylene, C$_6$-C$_{32}$ substituted arylalkylene, C$_1$-C$_{32}$ alkyleneamino, C$_1$-C$_{32}$ substituted alkyleneamino, with the proviso that if E does not comprise a repeating alkylene oxide moiety then E can further comprise a heteroatom selected from the group consisting of P, N, and O;
m is an integer independently selected from 2 to 100;
n is an integer independently selected from 1 or 2; and when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$, and further wherein at least one E does not comprise an ethylene moiety;

wherein t is an integer independently selected from 1, 2, or 3; and $k \leq (m/t)+1$;

such that the total number of cationic charges balances the total number of anionic charges in the organopolysiloxane molecule; and wherein the organopolysiloxane has a charge density of from 0.75 meq/g to 12 meq/g;

wherein from 90% to 100% of the amines present in the molecule are quaternized.

2. The organopolysiloxane according to claim 1 wherein w is an integer from 2 to 50.

3. The organopolysiloxane according to claim 1, wherein each E is independently selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkyleneamino, and $C_1$-$C_{32}$ substituted alkyleneamino.

4. The organopolysiloxane according to claim 1 having a charge density of from 0.04 meq/g to 4 meq/g.

5. The organopolysiloxane according to claim 1, wherein w is equal to 2.

6. The organopolysiloxane according to claim 1, wherein x is an integer from 10 to 4,000.

7. The organopolysiloxane according to claim 1, wherein x is an integer from 40 to 2,000.

8. The organopolysiloxane according to claim 1, wherein w is equal to 2, x is an integer from 20 to 1,000, and y and z are 0.

9. The organopolysiloxane according to claim 1, wherein each X is a divalent radical independently selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkyleneamino, and $C_1$-$C_{32}$ substituted alkyleneamino.

10. The organopolysiloxane according to claim 1, wherein each X is a divalent radical independently selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, and $C_6$-$C_{32}$ substituted arylalkylene.

11. The organopolysiloxane according to claim 1, wherein $A^{-t}$ is selected from the group consisting of $Cl^-$, $Br^-$, $I^-$, methylsulfate, toluene sulfonate, carboxylate, phosphate, hydroxide, acetate, formate, carbonate, nitrate, and combinations thereof.

12. The organopolysiloxane according to claim 1, wherein $A^{-t}$ is selected from the group consisting of $Cl^-$, $Br^-$, $I^-$, methylsulfate, toluene sulfonate, carboxylate, phosphate and combinations thereof.

13. The organopolysiloxane according to claim 1, wherein each E is a divalent radical independently selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene $C_1$-$C_{32}$ alkyleneamino, and $C_1$-$C_{32}$ substituted alkyleneamino.

14. The organopolysiloxane according to claim 1, wherein each E is a divalent radical independently selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, and $C_6$-$C_{32}$ substituted arylalkylene.

15. The organopolysiloxane according to claim 1, wherein each E comprises more than 3 carbon atoms.

16. The organopolysiloxane according to claim 1, wherein at least one E is selected from the group consisting of:

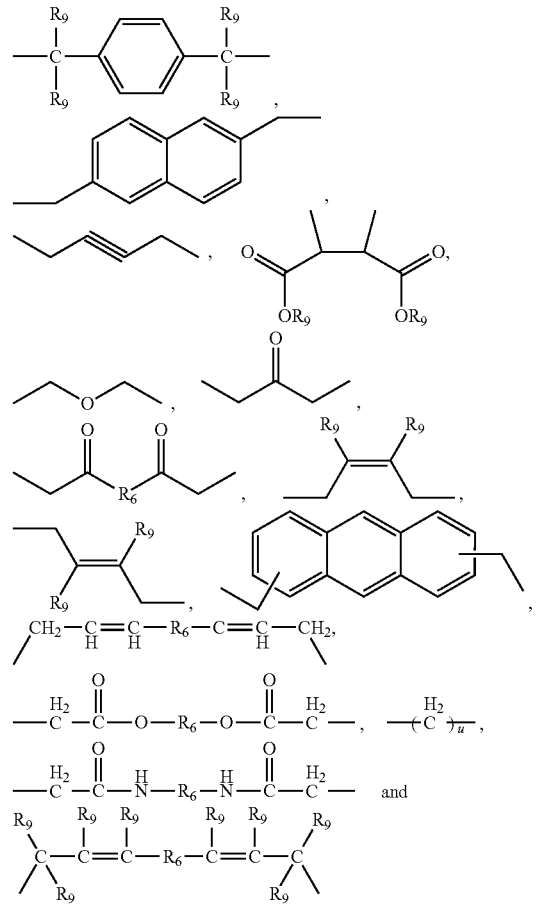

wherein:
each $R_6$ comprises a divalent radical independently selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkyleneamino, and $C_1$-$C_{32}$ substituted alkyleneamino, with the proviso that if $R_6$ does not comprise a repeating alkylene oxide moiety then $R_6$ can further comprise a heteroatom selected from the group consisting of P, N, and O;

each $R_9$ comprises an identical or different monovalent radical independently selected from the group consisting of H, $C_1$-$C_{32}$ alkyl, $C_1$-$C_{32}$ substituted alkyl, $C_5$-$C_{32}$ aryl, $C_5$-$C_{32}$ substituted aryl, $C_6$-$C_{32}$ alkylaryl, and $C_6$-$C_{32}$ substituted alkylaryl; and u is an integer independently selected from 3 to 32.

17. The organopolysiloxane according to claim 1, wherein at least one E radical is an ethylene radical.

18. The organopolysiloxane according to claim 1, wherein each $R_4$ is independently selected from the group consisting of H and $CH_3$.

19. The organopolysiloxane according to claim 1, wherein at least one $R_4$ is a methyl radical.

20. The organopolysiloxane according to claim 1, wherein for at least one $G_1$, $G_2$, or $G_3$, m is an integer independently selected from 2 to 50.

21. The organopolysiloxane according to claim 1, wherein for at least one $G_1$, $G_2$, or $G_3$, m is an integer independently selected from 2 to 25.

22. The organopolysiloxane according to claim 1, wherein for at least one $G_1$, $G_2$, or $G_3$, m is an integer independently selected from 2 to 10.

23. The organopolysiloxane according to claim 1, wherein for at least one $G_1$, $G_2$, or $G_3$, k is an integer independently selected from 0 to 101.

24. The organopolysiloxane according to claim 1, wherein for at least one $G_1$, $G_2$, or $G_3$, k is an integer independently selected from 2 to 50.

25. The organopolysiloxane according to claim 1, wherein y=z=0.

26. The organopolysiloxane according to claim 1, having a charge density of from 1 meq/g to 12 meq/g.

27. A cationic organopolysiloxane having the formula:

$$M_w D_x T_y Q_z$$

wherein:
M=[SiR$_1$R$_2$R$_3$O$_{1/2}$], [SiR$_1$R$_2$G$_1$O$_{1/2}$], [SiR$_1$G$_1$G$_2$O$_{1/2}$], [SiG$_1$G$_2$G$_3$O$_{1/2}$], or combinations thereof;
D=[SiR$_1$R$_2$O$_{2/2}$], [SiR$_1$G$_1$O$_{2/2}$], [SiG$_1$G$_2$O$_{2/2}$] or combinations thereof;
T=[SiR$_1$O$_{3/2}$], [SiG$_1$O$_{3/2}$] or combinations thereof;
Q=[SiO$_{4/2}$];
w=is an integer from 1 to (2+y+2z);
x=is an integer from 5 to 15,000;
y=is an integer from 0 to 98;
z=is an integer from 0 to 98;
$R_1$, $R_2$, and $R_3$ are each independently selected from the group consisting of H, OH, $C_1$-$C_{32}$ alkyl, $C_1$-$C_{32}$ substituted alkyl, $C_5$-$C_{32}$ aryl, $C_5$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy, $C_1$-$C_{32}$ alkylamino, and $C_1$-$C_{32}$ substituted alkylamino;
at least one of M, D, or T incorporates at least one moiety $G_1$, $G_2$, or $G_3$; and
$G_1$, $G_2$, and $G_3$ are each independently selected from the formula:

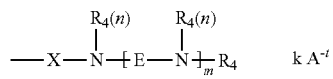

X comprises a divalent radical selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkyleneamino, $C_1$-$C_{32}$ substituted alkyleneamino with the proviso that if X does not comprise a repeating alkylene oxide moiety then X can further comprise a heteroatom selected from the group consisting of P, N, and O;
N=a nitrogen atom;
each $R_4$ comprises identical or different monovalent radicals independently selected from the group consisting of H, $C_1$-$C_{32}$ alkyl, $C_1$-$C_{32}$ substituted alkyl, $C_5$-$C_{32}$ aryl, $C_5$-$C_{32}$ substituted aryl, $C_6$-$C_{32}$ alkylaryl, and $C_6$-$C_{32}$ substituted alkylaryl;
E comprises a divalent radical selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkyleneamino, $C_1$-$C_{32}$ substituted alkyleneamino with the proviso that if E does not comprise a repeating alkylene oxide moiety then E can further comprise a heteroatom selected from the group consisting of P, N, and O;
m is an integer independently selected from 2 to 100;
n is an integer independently selected from 1 or 2; and
when at least one of $G_1$, $G_2$, or $G_3$ is positively charged, $A^{-t}$ is a suitable charge balancing anion or anions such that the total charge, k, of the charge-balancing anion or anions is equal to and opposite from the net charge on the moiety $G_1$, $G_2$ or $G_3$, and further wherein at least one E does not comprise an ethylene moiety;
wherein t is an integer independently selected from 1, 2, or 3; and k≤(m/t)+1;
such that the total number of cationic charges balances the total number of anionic charges in the organopolysiloxane molecule; and
wherein from 50% to 100% of the amines present in the molecule are quaternized;
wherein from 90% to 100% of the amines present in the molecule are quaternized, and wherein each E comprises more than 3 carbon atoms.

28. The organopolysiloxane according to claim 27 wherein w is an integer from 2 to 50.

29. The organopolysiloxane according to claim 27, wherein each E is independently selected from the group consisting of $C_4$-$C_{32}$ alkylene, $C_4$-$C_{32}$ substituted, alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_4$-$C_{32}$ alkyleneamino, and $C_4$-$C_{32}$ substituted alkyleneamino, ring-opened epoxide, and ring-opened glycidyl.

30. The organopolysiloxane according to claim 27 having a charge density of from 0.04 meq/g to 12 meq/g.

31. The organopolysiloxane according to claim 27 having a charge density of from 0.04 meq/g to 4 meq/g.

32. The organopolysiloxane according to claim 27 having a charge density of from 1 meq/g to 12 meq/g.

33. The organopolysiloxane according to claim 27, wherein w is equal to 2.

34. The organopolysiloxane according to claim 27, wherein x is an integer from 10 to 4,000.

35. The organopolysiloxane according to claim 27, wherein x is an integer from 40 to 2,000.

36. The organopolysiloxane according to claim 27, wherein w is equal to 2, x is an integer from 20 to 1,000, and y and z are 0.

37. The organopolysiloxane according to claim 27, wherein each X is a divalent radical independently selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkyleneamino, and $C_1$-$C_{32}$ substituted alkyleneamino.

38. The organopolysiloxane according to claim 27, wherein each X is a divalent radical independently selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, and $C_6$-$C_{32}$ substituted arylalkylene.

39. The organopolysiloxane according to claim 27, wherein $A^{-t}$ is selected from the group consisting of Cl$^-$, Br$^-$, I$^-$, methylsulfate, toluene sulfonate, carboxylate, phosphate, hydroxide, acetate, formate, carbonate, nitrate, and combinations thereof.

40. The organopolysiloxane according to claim 27, wherein $A^{-t}$ is selected from the group consisting of $Cl^-$, $Br^-$, $I^-$, methylsulfate, toluene sulfonate, carboxylate, phosphate and combinations thereof.

41. The organopolysiloxane according to claim 27, wherein each E is a independently selected from the group consisting of $C_4$-$C_{32}$ alkylene, $C_4$-$C_{32}$ substituted, alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_4$-$C_{32}$ alkyleneamino, and $C_4$-$C_{32}$ substituted alkyleneamino.

42. The organopolysiloxane according to claim 27, wherein each E is a independently selected from the group consisting of $C_4$-$C_{32}$ alkylene, $C_4$-$C_{32}$ substituted, alkylene, $C_5$-$C_{32}$ arylene, $C_5$-$C_{32}$ substituted arylene, $C_6$-$C_{32}$ arylalkylene, and $C_6$-$C_{32}$ substituted arylalkylene.

43. The organopolysiloxane according to claim 27, wherein at least one E is selected from the group consisting of:

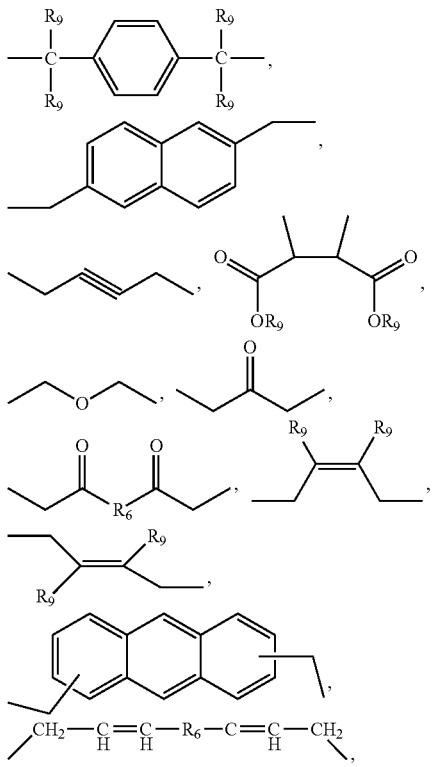

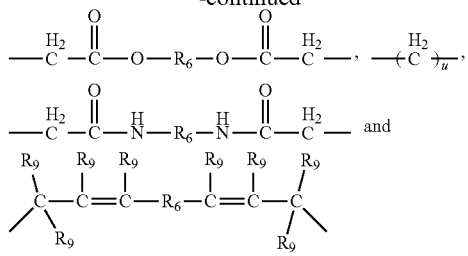

wherein:
each $R_6$ comprises a divalent radical independently selected from the group consisting of $C_1$-$C_{32}$ alkylene, $C_1$-$C_{32}$ substituted alkylene, $C_5$-$C_{32}$ arylene, $C_5$-$C_{32}$ substituted arylene, $C_6$-$C_{32}$ arylalkylene, $C_6$-$C_{32}$ substituted arylalkylene, $C_1$-$C_{32}$ alkyleneamino, and $C_1$-$C_{32}$ substituted alkyleneamino, with the proviso that if $R_6$ does not comprise a repeating alkylene oxide moiety then $R_6$ can further comprise a heteroatom selected from the group consisting of P, N, and O;

each $R_9$ comprises an identical or different monovalent radical independently selected from the group consisting of H, $C_1$-$C_{32}$ alkyl, $C_1$-$C_{32}$ substituted alkyl, $C_5$-$C_{32}$ aryl, $C_5$-$C_{32}$ substituted aryl, $C_6$-$C_{32}$ alkylaryl, and $C_6$-$C_{32}$ substituted alkylaryl; and u is an integer independently selected from 4 to 32.

44. The organopolysiloxane according to claim 27, wherein each $R_4$ is independently selected from the group consisting of H and $CH_3$.

45. The organopolysiloxane according to claim 27, wherein at least one $R_4$ is a methyl radical.

46. The organopolysiloxane according to claim 27, wherein for at least one $G_1$, $G_2$, or $G_3$, m is an integer independently selected from 2 to 50.

47. The organopolysiloxane according to claim 27, wherein for at least one $G_1$, $G_2$, or $G_3$, m is an integer independently selected from 2 to 25.

48. The organopolysiloxane according to claim 27, wherein for at least one $G_1$, $G_2$, or $G_3$, m is an integer independently selected from 2 to 10.

49. The organopolysiloxane according to claim 27, wherein for at least one $G_1$, $G_2$, or $G_3$, k is an integer independently selected from 0 to 101.

50. The organopolysiloxane according to claim 27, wherein for at least one $G_1$, $G_2$, or $G_3$, k is an integer independently selected from 2 to 50.

51. The organopolysiloxane according to claim 27, wherein $y=z=0$.

* * * * *